United States Patent [19]

Lee et al.

[11] Patent Number: 5,092,332

[45] Date of Patent: Mar. 3, 1992

[54] STEROID ELUTING CUFF ELECTRODE FOR PERIPHERAL NERVE STIMULATION

[75] Inventors: Philip Lee, Woodbury; Kenneth Stokes, Brooklyn Park; James Gates, Maple Grove; Gary Johnson, Ramsey, all of Minn.

[73] Assignee: Medtronic, Inc., Minneapolis, Minn.

[21] Appl. No.: 483,455

[22] Filed: Feb. 22, 1990

[51] Int. Cl.$^5$ ............................ A61B 5/04; A61N 1/05
[52] U.S. Cl. .................................... 128/642; 128/784; 128/785
[58] Field of Search ..................... 128/784–786, 128/419 P, 419 C, 642, 50

[56] References Cited

U.S. PATENT DOCUMENTS

| | | |
|---|---|---|
| 1,662,446 | 3/1928 | Wappler . |
| 3,421,511 | 1/1969 | Schwartz . |
| 3,654,933 | 4/1972 | Hagfors . |
| 4,281,668 | 8/1981 | Richter et al. ............... 128/784 |
| 4,341,221 | 7/1982 | Testerman . |
| 4,506,680 | 3/1985 | Stokes . |
| 4,577,642 | 3/1986 | Stokes . |
| 4,602,624 | 7/1986 | Naples et al. ............... 128/784 |
| 4,606,118 | 8/1986 | Cannon et al. . |
| 4,711,251 | 12/1987 | Stokes . |

Primary Examiner—Lee S. Cohen
Attorney, Agent, or Firm—Harold R. Patton; Terry L. Wiles; John L. Rooney

[57] ABSTRACT

An improved electrode for establishing electrical contact with a nerve of a patient. This electrical contact may be used to sense neural activity on the nerve or to artificially stimulate it to perform various medical treatments. The electrode has an outer cuff of an insulating material which is sutured around the nerve to be contacted. A drug impregnated layer of material is positioned inside of the outer cuff. This material is a polymeric matrix which permits the drug to leach out at a predetermined rate. The drug is a steroid such as dexamethasone sodium phosphate. The actual electrical contact is produced by metallic foil which is positioned on the surface of the drug impregnated layer of material which is located inside of the cuff. An insulated lead electrically couples the metallic foil to an electronic circuit located remote from the nerve. The leaching out of the drug serves to control irritation, swelling, and impedance of the nerve/electrode interface.

8 Claims, 4 Drawing Sheets

STEROID ELUTING CUFF ELECTRODE FOR PERIPHERAL NERVE STIMULATION

CROSS-REFERENCE TO COPENDING APPLICATIONS

This application is related to Ser. No. 07/446,594, filed Dec. 6, 1989, now U.S. Pat. No. 3,009,228, entitled "Steroid Eluting Intramuscular Lead" and Ser. No. 07/446,865, filed Dec. 6, 1989, now U.S. Pat. No. 3,031, entitled "Nerve Electrode with Biological Substrate", both of which assigned to the assignee of this application.

BACKGROUND OF THE INVENTION

1. Field of the Invention:

The present invention generally relates to implantable medical devices and more particularly relates to electrodes for electrically coupling to nerve tissue.

2. Description of the Prior Art:

The use of electrodes to monitor electrical activity and stimulate body tissue is quite old. U.S. Pat. No. 1,662,446 issued to R. H. Wappler teaches an early electrode system. The Wappler electrode is used for acute stimulation only, and is not implantable.

An early stimulation electrode which is chronically implantable is taught by S. I. Schwartz, et al in U.S. Pat. No. 3,421,511, herein incorporated by reference. U.S. Pat. No. 3,654,933 issued to Hagfors, herein incorporated by reference, teaches an improved stimulation electrode for chronic implantation. Clinical experience with the electrodes taught by Schwartz, et al and Hagfors may produce excess irritation in certain applications. This irritation results in swelling of the nerve tissue and ultimately an unacceptable increase in impedance of the nerve tissue/electrode interface.

U.S. Pat. No. 4,341,221 issued to Testerman teaches an improved nerve electrode for chronic implantation which uses gel electrodes. While offering some improvement, excess irritation is yet experienced in some patients.

Cardiac pacing leads which sense and stimulate activity in the myocardial muscle tissue have been in use for some time. U.S. Pat. No. 4,711,251 issued to Stokes teaches an endocardial pacing lead having steroid drug embedded in the distal tip. U.S. Pat. Nos. 4,506,680; 4,577,642; and 4,606,118 teach similar endocardial pacing leads, all of which have an embedded steroid drug. U.S. Statutory Invention Registration No. H356 discloses a pacing lead suitable for epicardial application which elutes a steroid drug. Because cardiac pacing leads establish electrical contact with muscle tissue rather than nerve tissue, the total contact area is extremely small to increase current density. Therefore, the area of muscle tissue to be treated by the embedded drug is so small that only minute quantities of drug need be eluted.

SUMMARY OF THE INVENTION

The present invention overcomes the disadvantages of the prior art by directly treating the irritation of the nerve tissue caused by contact with the electrode.

This area is treated with an anti-inflammatory drug such as a steroid which is topically applied at a predetermined chronic rate.

The steroid drug is embedded in a polymeric matrix which permits the drug to leach out at the desired rate. The polymeric matrix is a layer of material which is applied to the outer substrate of the electrode system. The metallic electrode elements are positioned on the polymeric matrix layer opposite the outer substrate.

The outer substrate is wrapped about the nerve at the desired location, and the edges of the outer substrate are sutured to hold the electrode in place. The metallic electrode elements contact the nerve tissue directly and are electrically coupled to an insulated lead which couples to remote electronic circuitry. The polymeric matrix thus treats the entire surface area of the nerve tissue which is wrapped with the cuff formed by the sutured outer substrate.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
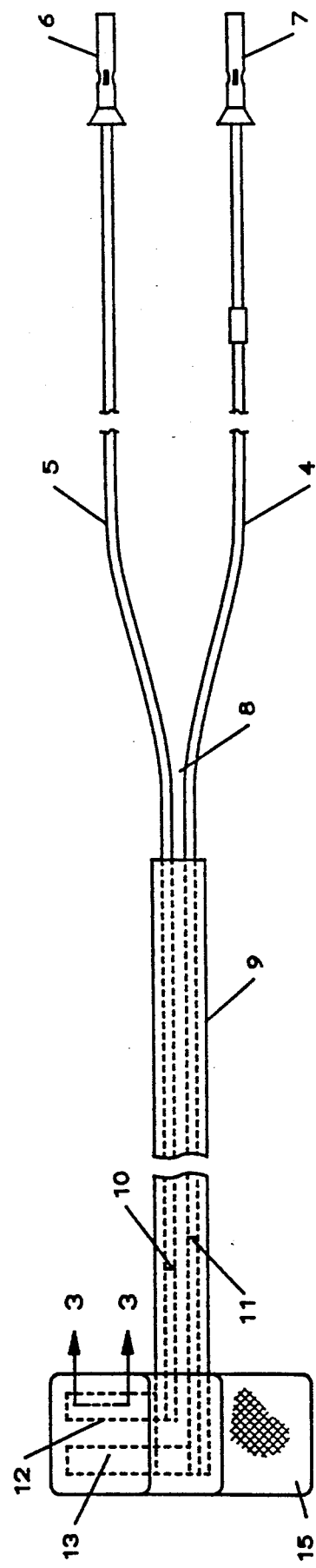
FIG. 1 is a plan view of a neurological lead suitable for chronic implantation incorporating the present invention.

FIG. 1 is a plan view of a neurological lead suitable for chronic implantation incorporating the present invention. The proximal end of the lead has connector pins 6 and 7 which establish electrical contact with electronic circuitry remote from the site of the nerve. This electronic circuitry (not shown) may include sensing and monitoring functions and/or pulse generation functions for stimulation. Connector pins 6 and 7 are electrically coupled to insulated wires 4 and 5 which join at point 8 and are covered distally by outer insulating sheath 9. The dashed lines show the location 10 and 11 of the extension of wires 4 and 5.

By way of illustration, outer substrate 15 is an insulator of a flexible polymeric material having a length of about ⅜ inch and a width of about ¼ inch. It is fixedly attached to outer insulating sheath 9. Attached to outer insulating sheath 9 is polymeric matrix layer 16 which is not shown in this illustration. The position of metallic foils 12 and 13 are shown by the dashed lines.

Figure 2:
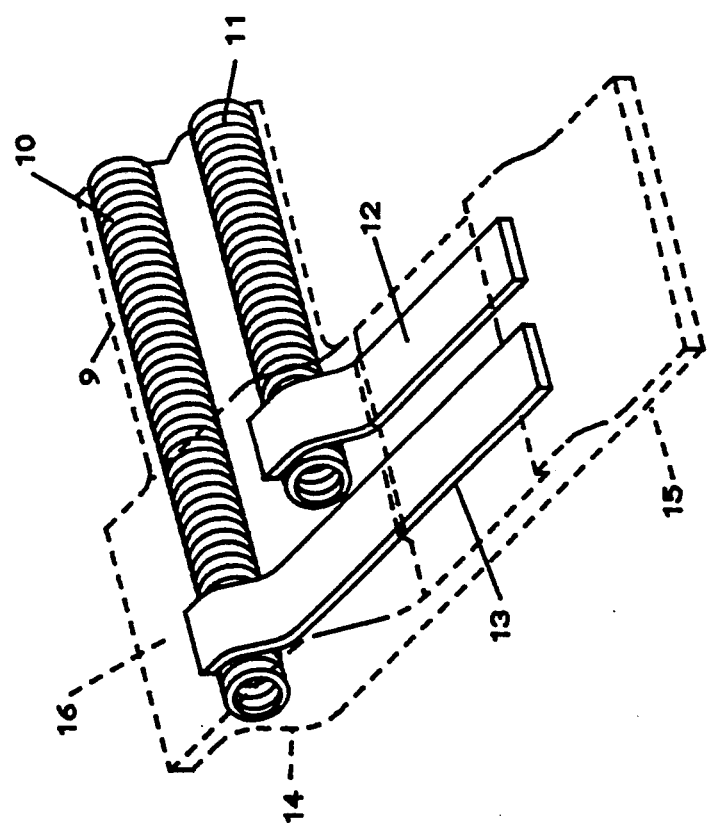
FIG. 2 is a closeup view of the electrode which contacts the nerve tissue.

FIG. 2 is a closeup view of the electrode structure as seen from the side which directly contacts the nerve tissue. Extension 10 is a conductor coil which is electrically coupled to metallic foil 13. Similarly, extension 1; is a conductor coil which is electrically coupled to metallic foil 12. Polymeric matrix layer 16 is shown as attached to the entire surface of outer substrate 15. Molded portion 14 of outer substrate 15, because of its increased thickness, tends to ensure ease of implantation by causing bending of outer substrate 15 at the desired points.

Polymeric matrix layer 16 may be fabricated in a variety of ways. By way of example and not to be deemed as limiting of the present invention, a preferred mode is a mixture of 0.2 milligrams of dexamethesone sodium phospate with 0.5 cubic centimeters of silastic medical adhesive. The mixture is molded to the desired shape and allowed to cure. After curing polymeric matrix layer 16 is fixedly attached to outer substrate 15 with silastic medical adhesive.

Figure 3:
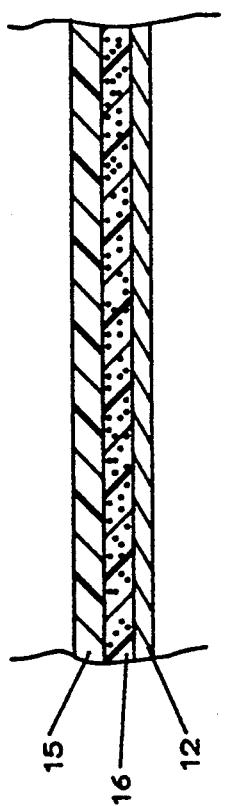
FIG. 3 is a closeup view of a cross-section of the nerve electrode.

FIG. 3 is a closeup of a cross-section of the electrode structure. Polymeric matrix layer 16 is attached to outer substrate 15. Metallic foil 12 is attached to polymeric matrix layer 16 using silastic medical adhesive. Metallic foil 13 (not shown) is similarly attached.

Figure 4:
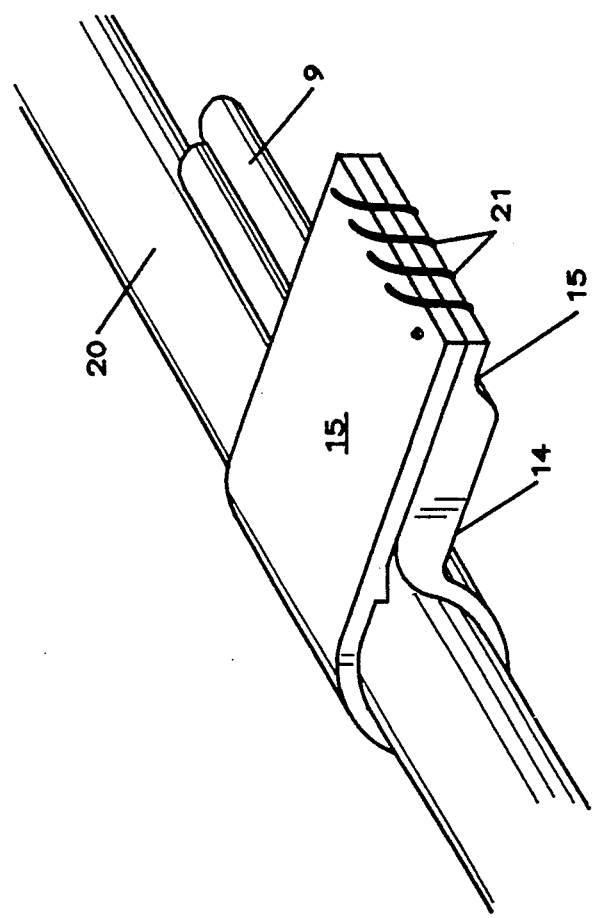
FIG. 4 is a view of the nerve electrode as sutured into place for chronic implantation about a nerve.

FIG. 4 is a view of the electrode assembly after it has been sutured into place for chronic implantation. Outer substrate 15 is wrapped about nerve 20 as shown. It is fixedly attached using sutures 21 at the edges of outer substrate 15. Molded portion 14 is shown as ensuring that outer substrate 15 is wrapped in the proper way. Outer insulating sheath 9 is shown as proceeding proximally from the electrode assembly parallel to nerve 20.

Having thus described the preferred embodiments, those of skill in the art will be readily able to apply the present invention without departing from the scope of the claims which are hereto attached.

We claim:

1. A nerve electrode comprising:
   a. substrate means for coupling to said nerve;
   b. means attached to said substrate means for chronically chemically treating irritation of said nerve;
   c. conductive electrode means attached to said chronically chemically treating means for electrically coupling to said nerve; and
   d. insulated electrical lead coupled to said conductive electrode means to couple said conductive electrode means to a remote electronic circuit.

2. A nerve electrode according to claim 1 wherein said substrate means is a flexible insulator.

3. A nerve electrode according to claim 2 wherein said chronically chemically treating means covers one surface of said substrate means.

4. A nerve electrode according to claim 3 wherein said chronically chemically treating means is a polymeric matrix containing a steroid drug.

5. A nerve electrode according to claim 4 wherein said steroid drug is dexamethasone sodium phosphate.

6. A nerve electrode according to claim 5 wherein said polymeric matrix further comprises silastic medical adhesive.

7. A nerve electrode according to claim 6 wherein said substrate means has a length of ⅜ inch and a width of ¼ inch.

8. A method of treating chronic irritation of nerve tissue coupled to a neurological electrode comprising:
   a. attaching a material containing an elutable steroid drug to said neurological electrode and in contact with said nerve tissue; and
   b. permitting said steroid drug to leach out of said material and into said nerve tissue.

* * * * *

UNITED STATES PATENT AND TRADEMARK OFFICE
CERTIFICATE OF CORRECTION

PATENT NO. : 5,092,332
DATED : March 3, 1992
INVENTOR(S) : Philip Lee, et al.

It is certified that error appears in the above-indentified patent and that said Letters Patent is hereby corrected as shown below:

Column 2, Line 57, delete "extension 1;", and insert in its place --extension 11;--.

Column 1, Line 8, delete "3,009,228", and insert in its place --5,009,229--.

Column 1, Line 10, delete "3,031,", and insert in its place --5,031,621--.

Signed and Sealed this

Twenty-seventh Day of September, 1994

Attest:

BRUCE LEHMAN

Attesting Officer          Commissioner of Patents and Trademarks